US011938032B2

United States Patent
Rivera, Jr.

(10) Patent No.: US 11,938,032 B2
(45) Date of Patent: Mar. 26, 2024

(54) PROSTHETIC IMPLANT REMOVAL TOOL AND ASSOCIATED METHOD

(71) Applicant: Simplex Designs, LLC, Duluth, GA (US)

(72) Inventor: Jose S. Rivera, Jr., Naples, FL (US)

(73) Assignee: SIMPLEX DESIGNS, LLC, Duluth, GA (US)

( * ) Notice: Subject to any disclaimer, the term of this patent is extended or adjusted under 35 U.S.C. 154(b) by 586 days.

(21) Appl. No.: 17/127,006

(22) Filed: Dec. 18, 2020

(65) Prior Publication Data

US 2022/0125591 A1 Apr. 28, 2022

Related U.S. Application Data

(63) Continuation-in-part of application No. 16/431,879, filed on Jun. 5, 2019, now Pat. No. 11,191,651.

(51) Int. Cl.
*A61F 2/36* (2006.01)
*A61B 17/92* (2006.01)
(Continued)

(52) U.S. Cl.
CPC ............ *A61F 2/3609* (2013.01); *A61B 17/92* (2013.01); *A61F 2/30771* (2013.01);
(Continued)

(58) Field of Classification Search
CPC .... A61F 2/4603; A61F 2/4607; A61B 17/155; A61B 17/16; A61B 17/164;
(Continued)

(56) References Cited

U.S. PATENT DOCUMENTS 4,222,382 A 9/1980 Antonsson et al.
6,790,211 B1 * 9/2004 McPherson ........... A61F 2/4607
606/169
(Continued)

FOREIGN PATENT DOCUMENTS

GB 2560956 A 10/2018
WO 92/22259 A2 12/1992
(Continued)

OTHER PUBLICATIONS

Chinese Office Action dated Jun. 13, 2022, in corresponding Chinese Application No. 202080054684.7.
(Continued)

*Primary Examiner* — Matthew J Lawson
(74) *Attorney, Agent, or Firm* — XSENSUS LLP

(57) ABSTRACT

A tool and an associated method for removing a prosthetic implant includes a lateral tool, a first impact tool secured to the lateral tool, a medial tool, and a second impact tool. Although the tool can be used to remove a variety of different prosthetic implants, it finds particular application in the removal of femoral implants. Both lateral and medial tools are utilized. The lateral tool includes a generally arcuate shape with upstanding sidewalls that define an arcuate interior. The lateral tool is thus dimensioned to follow the contour of the lateral side of a femoral implant. The medial tool includes opposing side walls that define an interior opening. The opening is sized to receive the neck of the femoral implant, thereby allowing the tool to closely follow the medial bone/implant interface.

12 Claims, 12 Drawing Sheets

(51) Int. Cl.
   *A61F 2/30* (2006.01)
   *A61F 2/46* (2006.01)
(52) U.S. Cl.
   CPC ...... *A61F 2/4607* (2013.01); *A61B 2017/922* (2013.01); *A61F 2002/30841* (2013.01); *A61F 2002/3625* (2013.01)
(58) Field of Classification Search
   CPC ............ A61B 17/1604; A61B 17/1668; A61B 17/1732; A61B 17/1735; A61B 17/1742; A61B 17/1664
   See application file for complete search history.

(56) References Cited

U.S. PATENT DOCUMENTS

| | | | | |
|---|---|---|---|---|
| 2008/0188878 | A1* | 8/2008 | Young | A61B 17/1628 606/171 |
| 2010/0069909 | A1* | 3/2010 | Taylor | A61F 2/4607 606/82 |
| 2012/0089147 | A1* | 4/2012 | Kuczynski | A61B 17/155 606/88 |
| 2013/0226189 | A1 | 8/2013 | Young | |
| 2014/0371750 | A1* | 12/2014 | Klein | A61B 17/1604 606/79 |
| 2018/0206859 | A1* | 7/2018 | Pendleton | A61B 17/1637 |
| 2018/0280036 | A1 | 10/2018 | Agunloye et al. | |
| 2019/0336143 | A1* | 11/2019 | Wright | A61B 17/1778 |
| 2020/0261247 | A1* | 8/2020 | Stchur | A61F 2/4014 |
| 2021/0353432 | A1 | 11/2021 | Rivera, Jr. | |

FOREIGN PATENT DOCUMENTS

| | | |
|---|---|---|
| WO | 2020/247064 A1 | 12/2020 |
| WO | 2022/140801 A2 | 6/2022 |

OTHER PUBLICATIONS

Extended European Search Report dated Aug. 5, 2022, in corresponding European Application No. 20817983.8.
Extended European search report dated Jun. 15, 2023, in corresponding European patent Application No. 22740032.2, 8 pages.
Office Action dated Dec. 30, 2022, in corresponding Chinese patent Application No. 202080054684.7 with partial English translation, 4 pages.
International Search Report and Written Opinion dated Jun. 22, 2022, corresponding PCT/US 22/13102, 11 pages.
Rivera Surgical, "Watson Extraction System", YouTube demonstration, Oct. 23, 2020, available URL: https://www.youtube.com/watch?v=CrD5vsMujiA.

* cited by examiner

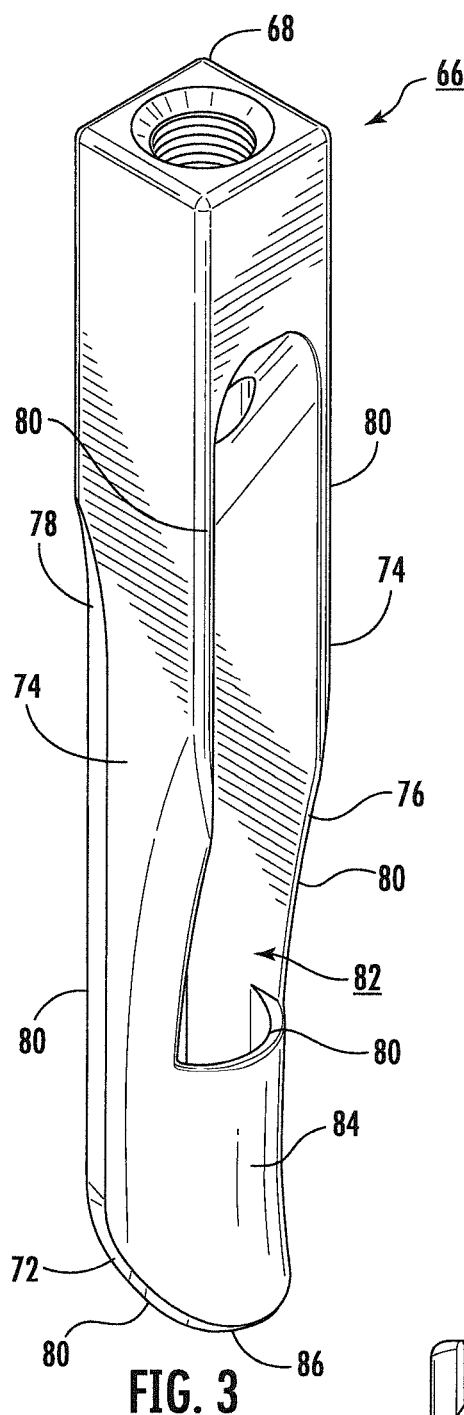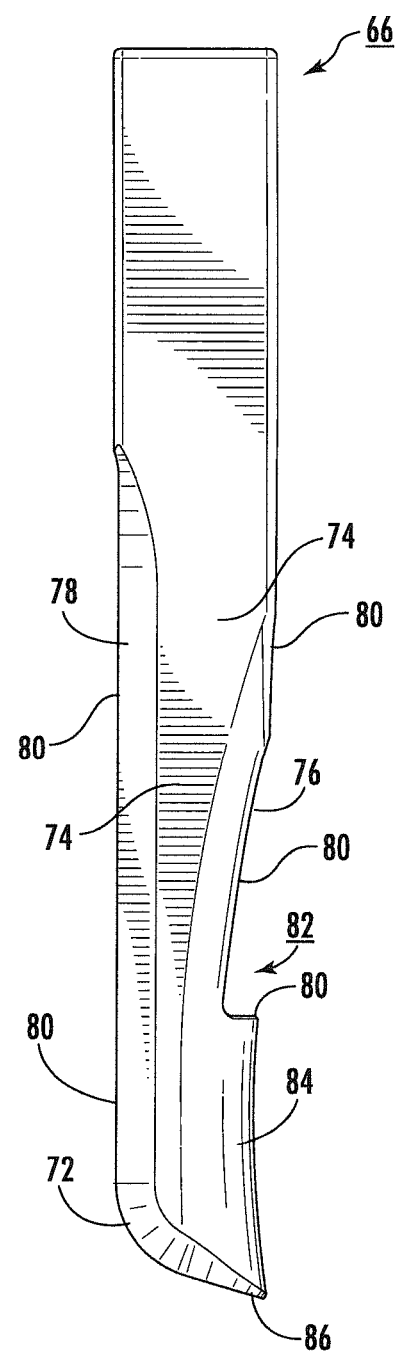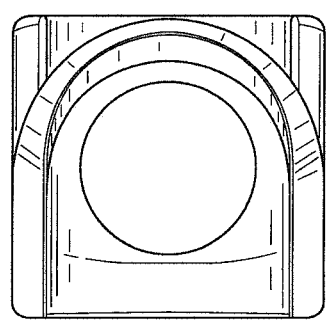
FIG. 3
FIG. 4
FIG. 5

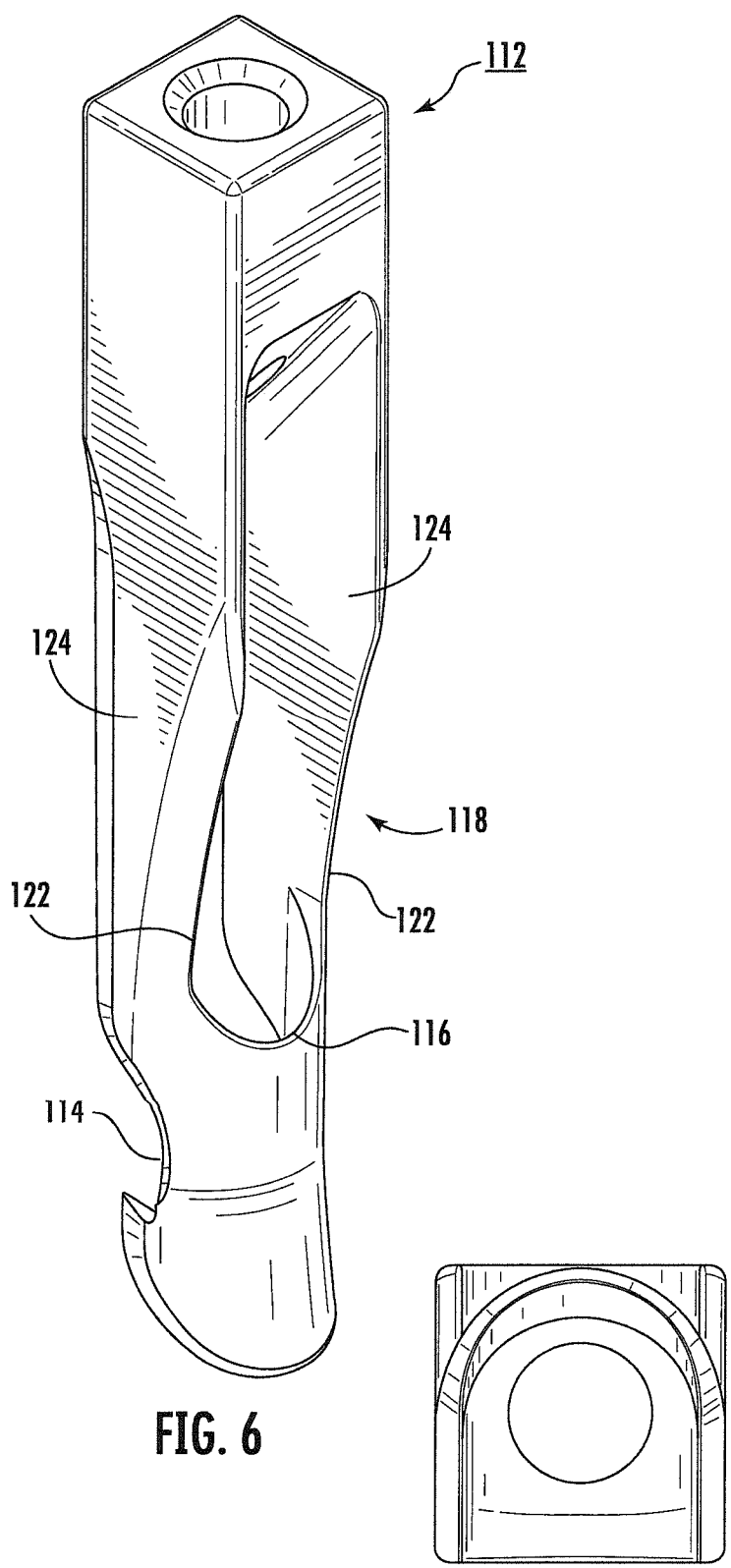
FIG. 6
FIG. 8
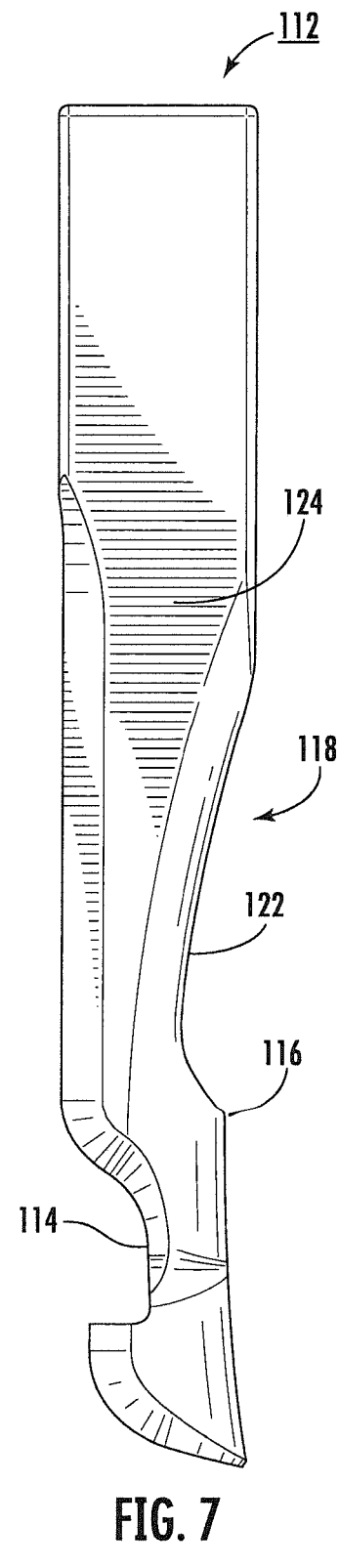
FIG. 7

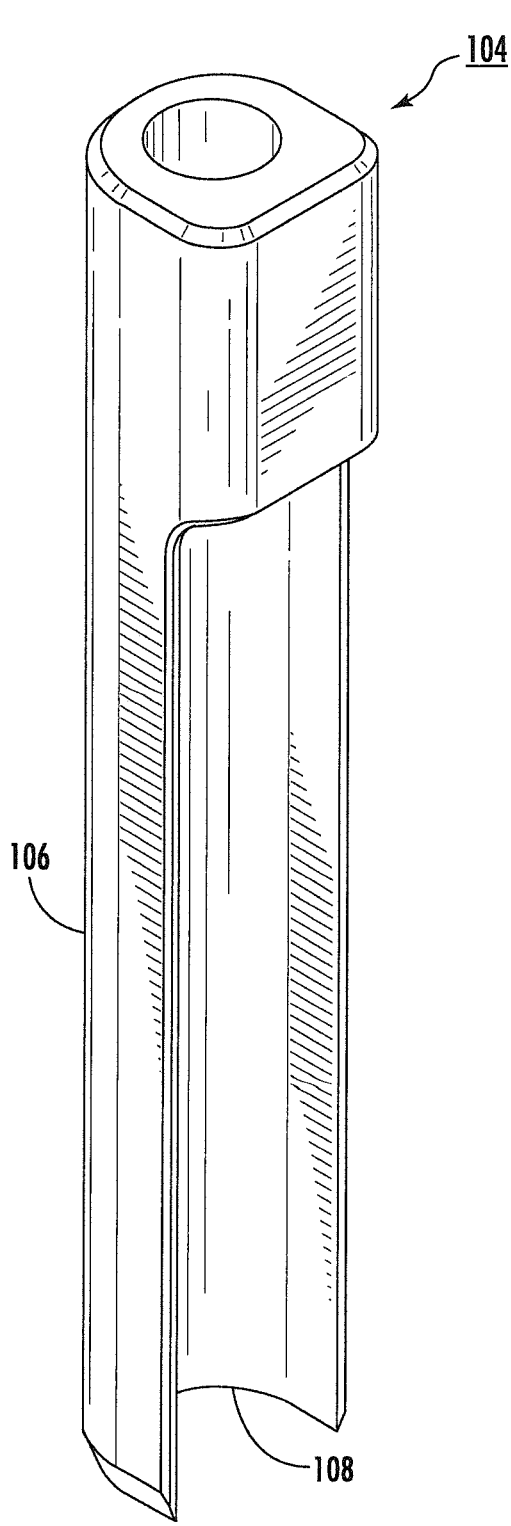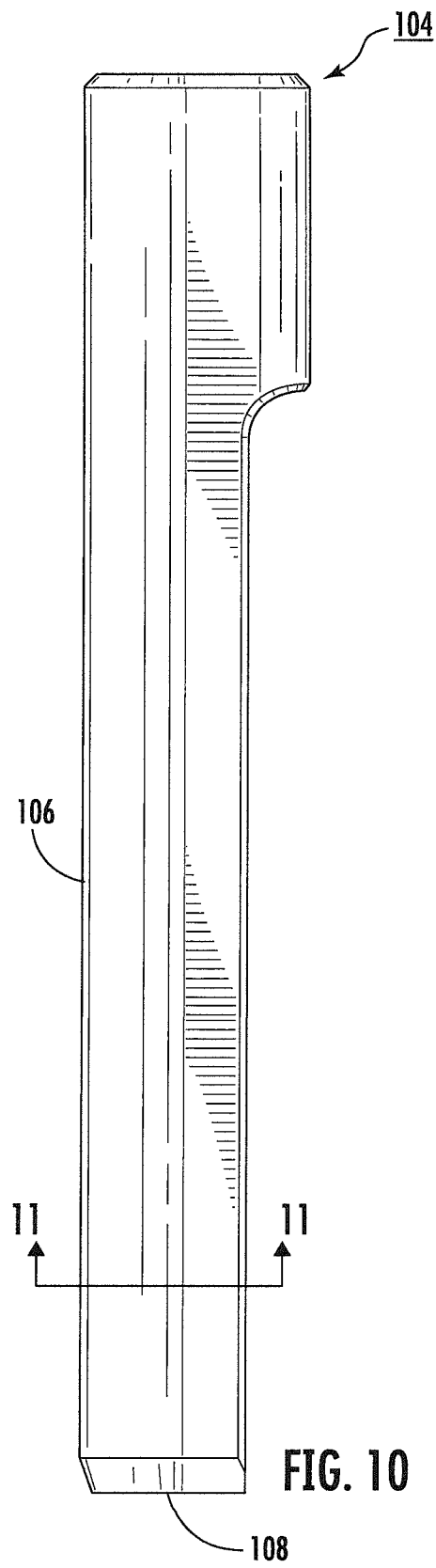
FIG. 9
FIG. 10

PROSTHETIC IMPLANT REMOVAL TOOL AND ASSOCIATED METHOD

CROSS REFERENCE TO RELATED APPLICATIONS

This application claims priority to and is a continuation-in-part of co-pending application Ser. No. 16/431,879 filed on Jun. 5, 2019 and entitled "Implant Removal Tool." The contents of this co-pending application are fully incorporated herein for all purposes.

TECHNICAL FIELD

This disclosure relates to a tool for removing a prosthetic implant. More particularly, the present disclosure relates to tools and associated methods for minimizing bone loss during the removal of a prosthetic.

BACKGROUND OF THE INVENTION

Joint arthroplasty is increasingly common in the United States and around the world. Arthroplasty can involve the complete or partial replacement of hips, knees, or shoulders. Of these, hip replacements are the most common form of surgery. During a hip replacement, the surgeon replaces the socket of the hip bone, known as the acetabulum, with an acetabular cup. The head of the femur is also replaced with a femoral implant. Femoral implants include a stem that is inserted into the superior end of the femur and an angled neck that extends upwardly. The neck mimics the natural neck of the femur and provides an attachment point for a head to be attached. These implants include coatings and texturing to promote bone growth to affix the implant to the femur and hip socket.

Most hip replacements last for approximately 25 years. After this time the acetabular cup and femoral implants may fail and need to be repaired or replaced. As life expectancy in general increases, people are living with artificial hips for longer periods of time. As a result, hip revision surgeries are on the rise. Hip revisions surgeries can be complicated and often pose more risk than the original hip replacement. During revision surgeries surgeons attempt to remove the existing implants while minimizing damage to surrounding bone and tissue. This is often a difficult task as implants are designed to join with the surrounding bone over time. Minimizing the loss of this bone during a revision helps the new implant to be properly affixed. It also reduces the length and cost of the revision surgery and further reduces recovery time. Efforts have been made over the years to provide tools that aid in the efficient removal of a prosthetic.

One example of this is disclosed in U.S. Pat. No. 9,867,628 to Macke. Macke relates to a method for the extraction of medical implants. In accordance with the method, a surgical cutting guide is attached to an implanted prosthesis. An osteotome is directed through a slot in the surgical cutting guide to a specified location at the interface between the prosthesis and the bone. The prosthesis is dislodged using the osteotome. The osteotome is then withdrawn through the slot. The slot can include a curvature to assist with minimize bone loss.

Another implant removal tool is disclosed by U.S. Pat. No. 6,187,012 to Masini. Masini discloses a guide means for directing a cutting tool into the interface between a prosthesis and the surrounding bone. The guide means is used to bring about a more controlled separation and removal of the prosthesis. The guide may be placed on the prosthesis itself or it may be placed on a separate component. In the case of a femoral implant, the guide can include tracks, channels, or groves that are oriented along the stem of the implant.

U.S. Pat. No. 5,257,995 to Umber discloses an apparatus for removing a prosthesis from a bone. The device includes a cutting tool having a cutting tip and an elongated shank that is designed to allow significant lateral flexing. A motor is included to provide rotational motion to the cutting tool. A handle is also provided that is designed to be held in the hand opposite of the cutting tool. The handle includes a bearing carrier with a hole for receiving the shank of the cutting tool. The surgeon manipulates the handle and cutting tool to cut a perimeter around the prosthesis.

A further example is illustrated in U.S. Pat. No. 10,751,070 to Pendleton. The Pendleton device has at least one blade connected to a handle. The shape of the blade conforms to a portion of the implant so that a cutting tip of the blade can be positioned in a desired position relative to the implant and the femur. Force is applied to the handle so that the cutting tip of the blade cuts through bone growth from the femur into the implant.

Although the background art illustrates various devices and techniques for removing prosthetics, all suffer from significant drawbacks. Namely, the devices of the background art rely upon the skill of the surgeon and do not include tools that adequately accommodate the shape of the prosthetic being removed or that otherwise minimizes bone loss. The implant removal tool of the present disclosure is aimed at overcoming these and other shortcomings present in the background art.

SUMMARY OF THE INVENTION

This disclosure relates to a tool and an associated method for the efficient removal of prosthetics.

The disclosed tool has several important advantages. For example, the tool is shaped to conform to the interface between the bone and the prosthetic. The tool may also include an opening to accommodate extensions of the prosthetic. All of this allows for the efficient removal of the prosthetic.

Both lateral and medial tools can be provided for separating the lateral and medial sides of the prosthetic from the surrounding bone.

The tools may be curved or angled to match the profile of the prosthetic, thereby allowing the tool to be inserted as closely as possible along bone/prosthetic interface.

The tools may also include an opening to accommodate the neck of a femoral implant, thereby allowing the tool to be inserted along the edge that is immediately adjacent to the stem.

The edges around the opening may be sharpened to cut the anterior and posterior sides of the implant while at the same time cutting along the medial aspect.

An advantage of the tools of the present disclosure is that they allow prosthetics to be removed efficiently and in a minimal amount of time.

A further advantage of the tools is that they allow prosthetics to be removed while minimizing the loss of existing bone.

Still yet a further advantage of the tools is that the efficient removal of the prosthetics greatly decreases recovery time.

Another advantage is that the efficient removal of prosthetics reduces both the need for anesthesia and operating room costs in general.

Various embodiments of the invention may have none, some, or all of these advantages. Other technical advantages of the present invention will be readily apparent to one skilled in the art.

BRIEF DESCRIPTION OF THE DRAWINGS

For a more complete understanding of the present disclosure and its advantages, reference is now made to the following descriptions, taken in conjunction with the accompanying drawings, in which:

FIG. 3 is a perspective view of a medial implant removal tool.

FIG. 4 is a side view of a medial implant removal tool.

FIG. 5 is a bottom view of the medial implant removal tool.

FIG. 6 is a perspective view of an alternative embodiment of the medial implant removal tool.

FIG. 7 is a side view of the alternative embodiment of the medial implant removal tool.

FIG. 8 is a bottom view of the alternative embodiment of the medial implant removal tool.

FIG. 9 is a perspective view of an alternative embodiment of the lateral implant removal tool.

FIG. 10 is a side view of an alternative embodiment of the lateral implant removal tool.

Similar reference numerals refer to similar parts throughout the several views of the drawings.

Parts List

20 Femoral Implant
22 Lateral Side of Implant
24 Medial Side of Implant
26 Stem of Implant
28 Femur
32 Textured Extent of Implant
34 Neck of Implant
36 Lateral Tool
38 Proximal End of Lateral Tool
42 Distal End of Lateral Tool
44 Threaded Aperture of Lateral Tool
46 Outer Wall of Lateral Tool
48 Arcuate Extent of Outer Wall
52 Lateral Anterior/Posterior Walls
54 Interior Area of Lateral Tool -continued Parts List 56 Angled Extent of Lateral Anterior or Posterior Wall
58 Curved Extent of Anterior/Posterior Side Wall
60 Sharpened Edges
62 Window in Lateral Anterior/Posterior Wall
64 Leading Edge of Lateral Tool
66 Medial Tool
68 Proximal End of Medial Tool
72 Distal End of Medial Tool
74 Opposing Side Walls of Medial Tool
76 Inner Sharpened Edge of Side Wall
78 Outer Edge of Anterior/Posterior Wall
80 Sharpened Edges
82 Opening in Medial Tool
84 Trough of Medial Tool
86 Leading Edge of Medial Tool
88 First Impact Tool
90 Weighted Slide
92 Threaded Extent of First Impact Tool
94 Guide of First Impact Tool
96 Second Impact Tool
98 Threaded Extent of Second Impact Tool
100 Weighted Slide
102 Guide of Second Impact Tool
104 Alternate Embodiment of Lateral Tool
106 Straight Edge of an Alternative Lateral Tool
108 Curved Leading Edge of an Alternative Lateral Tool
112 Alternate Embodiment of Medial Tool
114 Cut Out in the Alternative Medial Tool
116 U-shaped Sharpened Edge of Opening
118 Opening in the Alternative Medial Tool
120 Nut Securing Impact Tool

DETAILED DESCRIPTION OF THE DRAWINGS

The present disclosure relates to a tool and an associated method for removing a prosthetic implant. Although the tool can be used to remove a variety of different prosthetic implants, it finds particular application in the removal of femoral implants. In one embodiment, both lateral and medial tools are utilized. In a preferred but non-limiting embodiment, the lateral tool includes a generally arcuate shape with upstanding sidewalls that define an arcuate interior. The lateral tool is thus dimensioned to follow the contour of the lateral side of a femoral implant. The medial tool, in one embodiment, includes opposing side walls that define an interior opening. The opening is sized to receive the neck of the femoral implant, thereby allowing the tool to closely follow the medial bone/implant interface. The details of these tools, and the manner in which they can be employed, are discussed in greater detail hereinafter.

Figure 13:
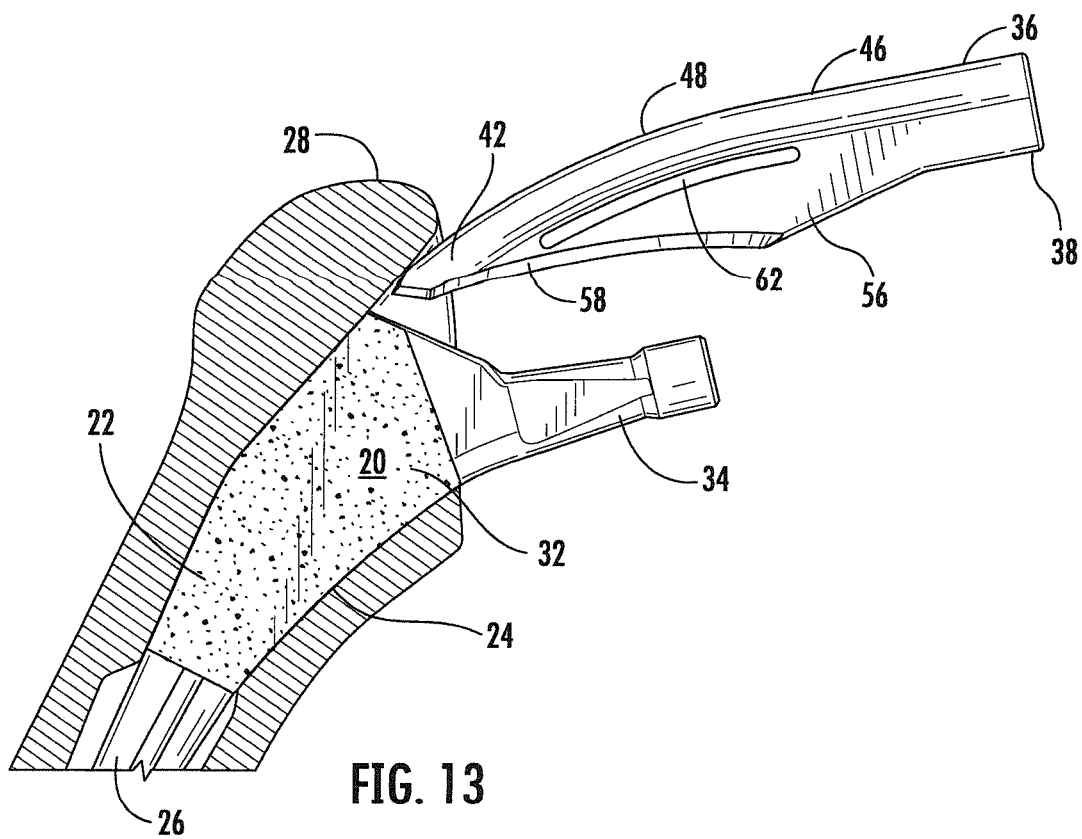
FIGS. 13-15 illustrate the insertion of the lateral implant removal tool.
Figure 14:
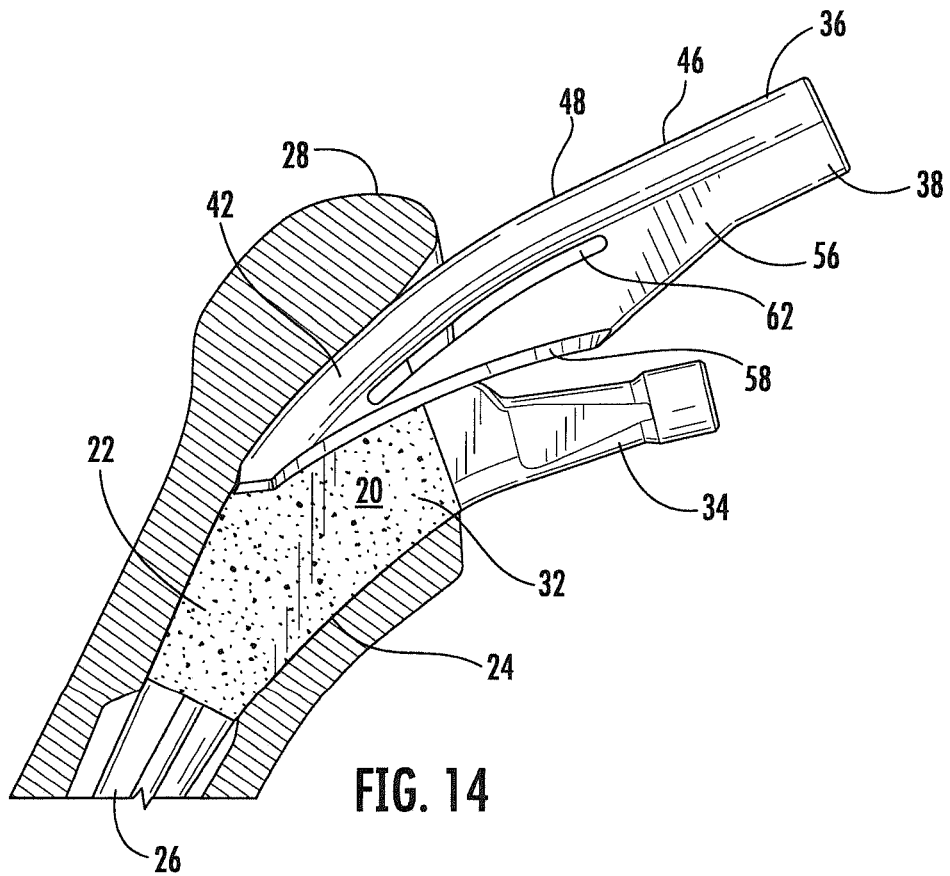
Figure 15:
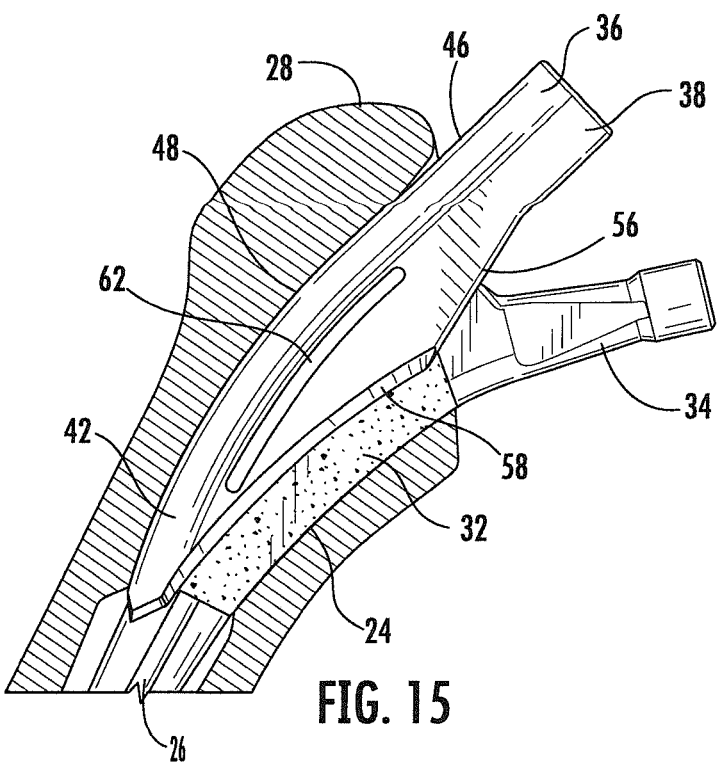
Figure 16:
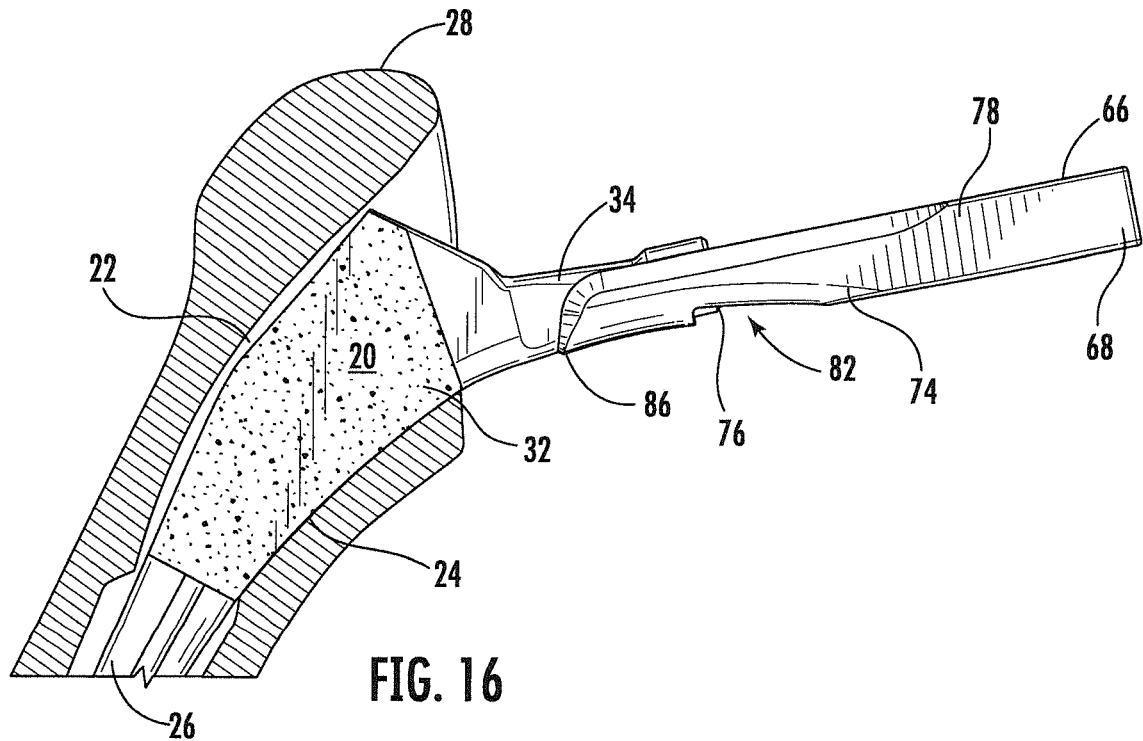
FIG. 16-17 illustrate the insertion of the medial implant removal tool.
Figure 17:
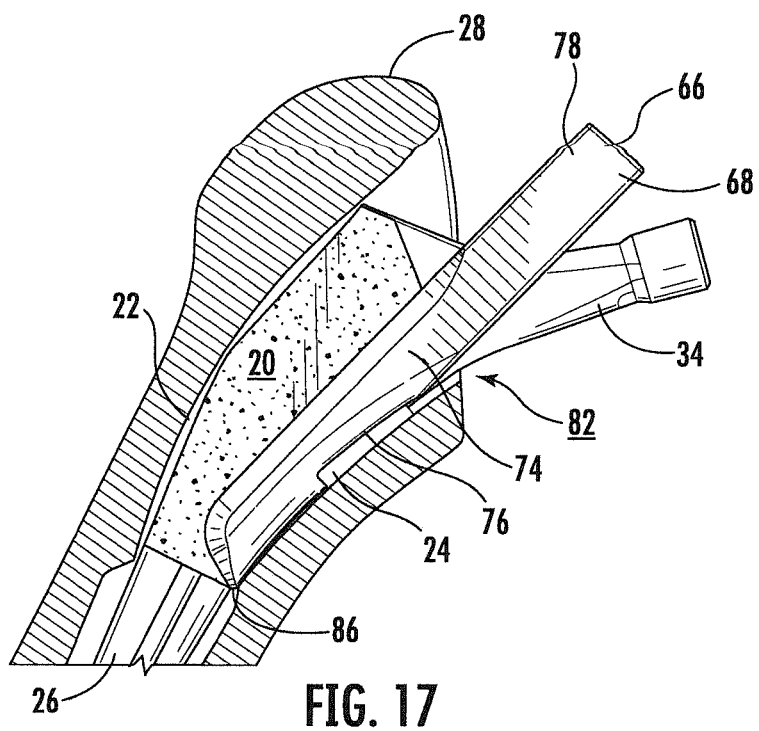

The disclosed tools are specifically designed to release an implanted prosthesis by closely following the bone/implant interface. The tools can be employed to remove a wide variety of different prosthetics, such as shoulder and hip implants. However, in the preferred embodiment, the tools are used to cut around, dislodge, and remove a femoral implant 20. As depicted in FIG. 13, these femoral implants 20 generally include a lateral (or outer) side 22 and a medial (or inner) side 24. Implant 20 further include a stem 26 that is inserted into the superior end of the femur bone 28. Various coatings and texturing can be employed for promoting bone growth and the grafting of the implant 20 to the femur 28. As illustrated, implant 20 includes a textured portion 32 at its upper portion where bone growth and proper affixation are most important. Femoral implant 20 also includes a neck 34 that is angled with respect to the body of the implant 20. A head (not shown) is then secured to the end of the neck 34, with the head ultimately being fitted into the acetabular cup (not shown).

Lateral Implant Removal Tool

Figure 1:
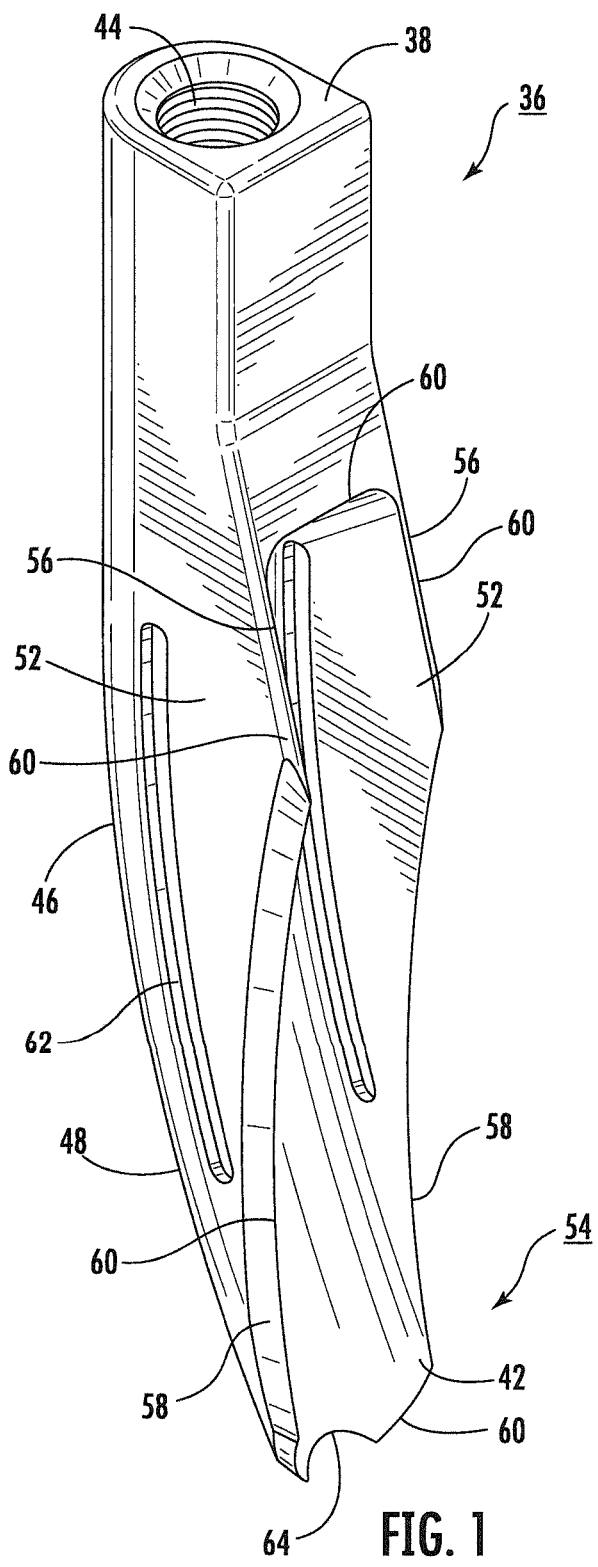
FIG. 1 is a perspective view of the lateral implant removal tool.
Figure 2:
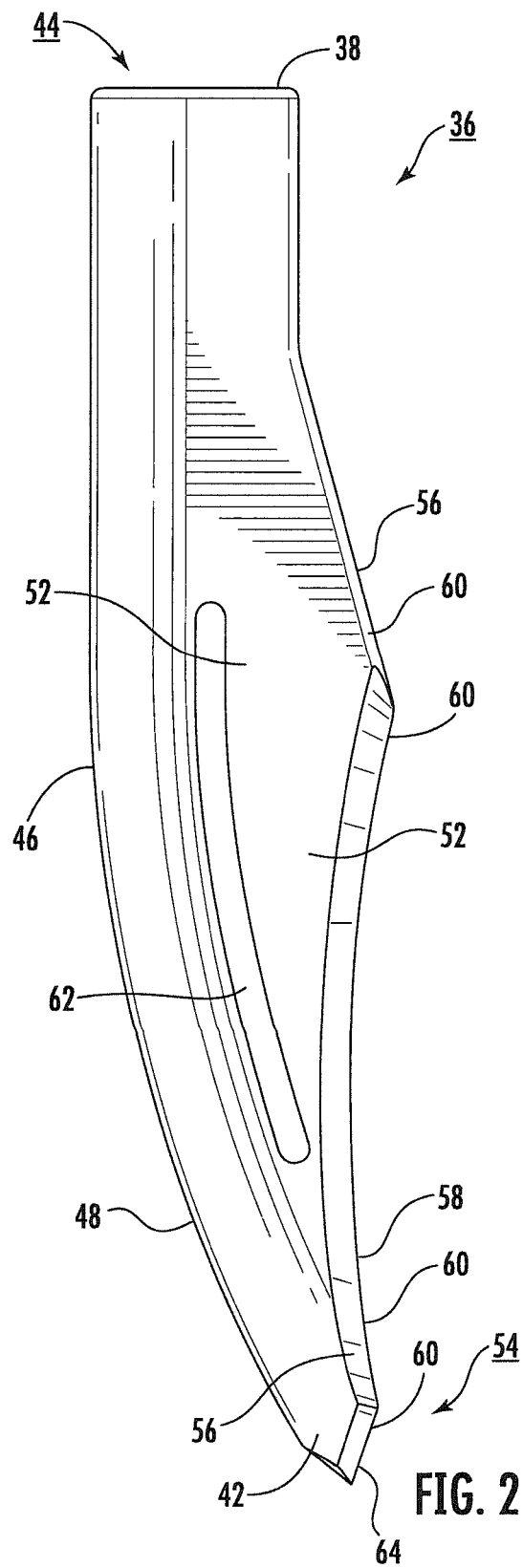
FIG. 2 is a side view of the lateral implant removal tool.

With reference to FIGS. 1-2, the lateral tool 36 includes proximal and distal ends (38 and 42), with the distal end 42 forming the leading edge that is inserted into femur 28. In order to allow tool 36 to be connected to an impact hammer (FIGS. 20-21), the proximal end 38 includes a threaded aperture 44. It is also possible to couple tool 36 to the impact hammer via a quick release mechanism. The use of the impact hammer is described in greater detail hereinafter. Although the size and shape of femoral implants vary, often times the lateral face 22 is curved to match the contour of the femur 28. As such, lateral tool 36 includes an outer wall 46 with an arcuate extent 48. Lateral tool 38 further includes opposing side walls 52. A curved or arcuate interior portion 54 is defined in the area between the opposing and outer walls 52. The shape and geometry of tool 36 may be changed to accommodate different types of prosthetics.

In one embodiment, each side wall 52 of lateral tool 36 includes a first angled extent 56 and a second curved extent 58. As illustrated, angled extent 56 is located near proximal end 38 of the tool 36 while the curved extent 58 is located at the distal end 42 of tool 36. The curved extents 58 of tool 36 are preferably angled and sharpened. All of the edges 60 surrounding interior portion 54 may be sharpened to facilitate insertion of tool 36. These sharpened edges 60 cut the bone growth along the bone/implant interface and otherwise allow for the insertion of tool 36. In order to allow the surgeon to gauge how far tool 36 has been inserted, a window 62 can be formed within one or both of the side walls 52. Distal end 42 of tool 36 optionally includes a curved and sharpened leading edge 64. Sharpened leading edge 64 and sharpened edges 60 allow lateral tool 36 to be inserted as closely as possible along the interface between the femur/implant. This, in turn, allows for the efficient removal of implant 20.

Medial Implant Removal Tool

With reference to FIGS. 3-4, the medial tool 66 includes proximal and distal ends (68 and 72) as well as opposing side walls 74. Side walls 74 are defined by inner and outer edges (76 and 78), and in a preferred embodiment, outer edges 78 of walls 74 are sharpened. However, unlike lateral tool 36, medial tool 66 is not closed. Rather, medial tool 66 includes a generally central opening 82. The purpose of opening 82 is described hereinafter. All of the inner and outer edges 80 surrounding central opening 82 are preferably sharpened. A U-shaped trough 84 with a sharpened leading edge 86 is formed at distal end 72 of medial tool 66. Medial tool 66 is adapted to be inserted between femur 28 and medial side 24 of femoral implant 20. All of the sharpened edges 80 assist with insertion, including outer edges 78, inner edges 76, and leading edge 86. Furthermore, neck 34 of femoral implant 20 is allowed to extend through opening 82 of medial tool 66. In this regard, opening 82 is specifically sized to accommodate neck 34 and end of implant 20. The sharpened edges surrounding opening 82 allows tool 66 to cut along the anterior and posterior sides as well as the medial aspect.

Method of Using Lateral and Medial Tools

Figure 20:
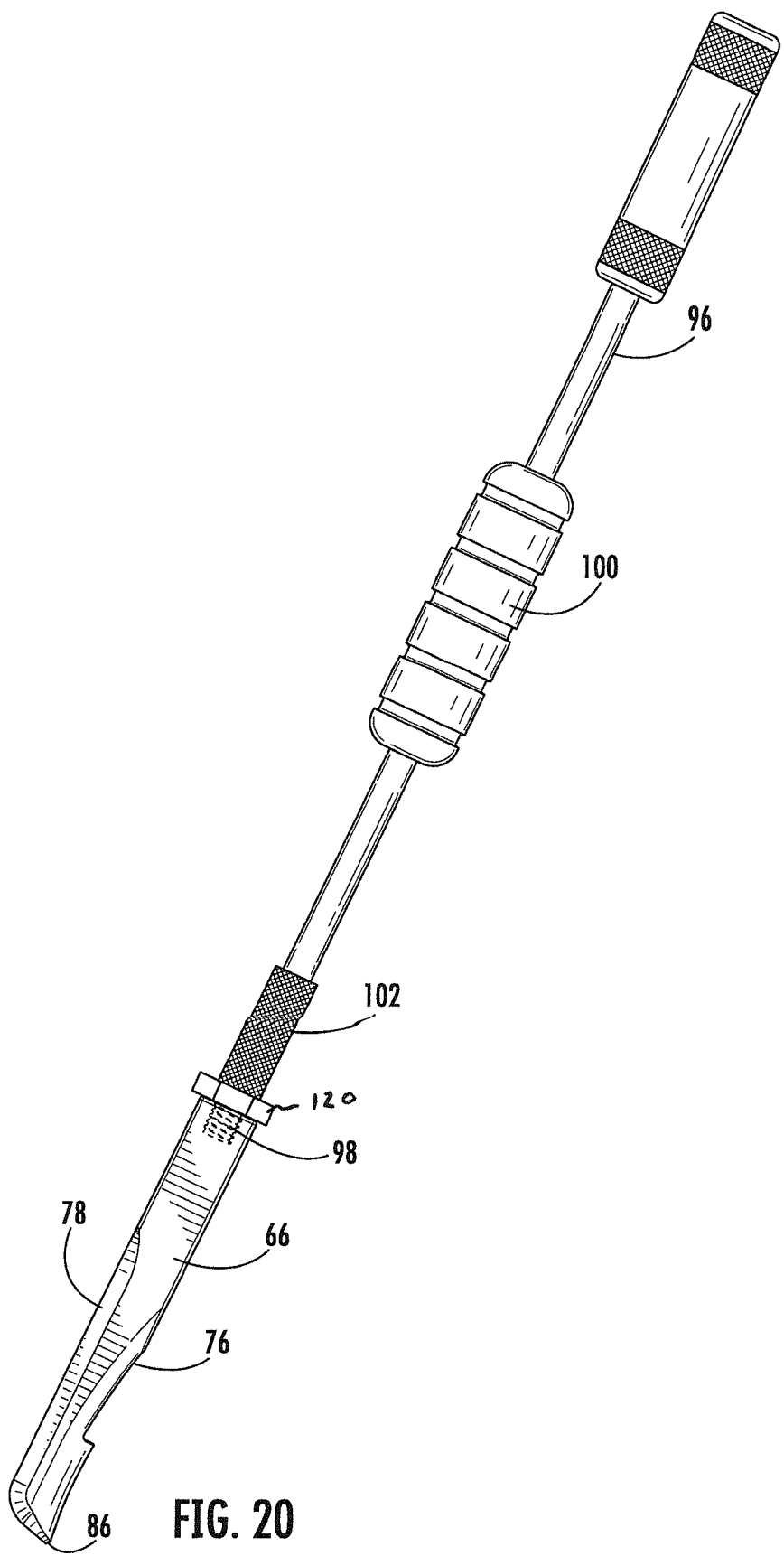
FIG. 20 is a view of an impact hammer secured to a medial tool.
Figure 21:
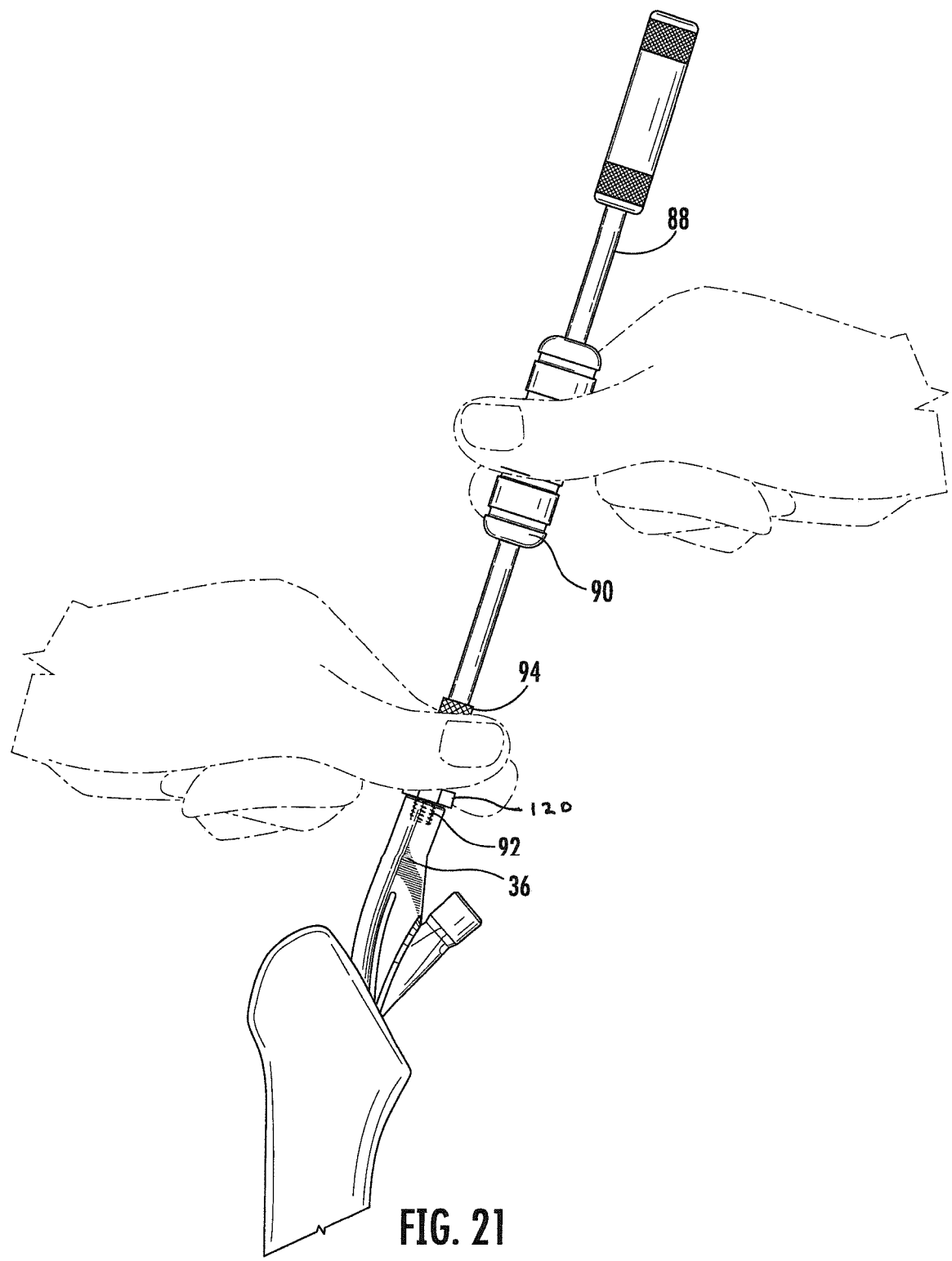
FIG. 21 is a view of an impact hammer being used to insert a lateral tool.

The method of using the tools (36 and 66) is next described in connection with FIGS. 13-19. Both lateral and medial tools (36 and 66) can be used in conjunction with one another to remove femoral implant 20. However, the present disclosure is not limited to the use of both tools (36 and 66) and the advantages of the invention can be realized by using either tool (36 or 66) individually. Each tool is inserted into the bone via an associated impact tool (88 and 96)(FIGS. 20-21). More specifically, a first impact tool 88 includes a threaded extent 92 that is secured to the threaded aperture 44 of lateral tool 36. A nut 120 can be secured immediately above threaded extent 92 to prevent the unintended rotation of impact tool 88 relative to lateral tool 36. Impact tool 88 includes a textured extent 94 that allows the surgeon to manipulate lateral tool 36 during insertion. The surgeon uses first impact tool 88 to guide the leading edge 64 and curved extents 58 of lateral tool 36 into femur 28. A weighted slide 90 is used as a hammer to apply force to the top of tool 36. During this insertion, bone growth between the femoral implant 20 and femur 28 is cut. Second impact tool 96 is substantially similar to the first impact tool 88 and is likewise used to position and insert medial tool 66. Namely, second impact tool 96 allows the leading edge 86 and outer and inner edges (78, 76) of the medial tool 66 (as well as all edges 80 surrounding opening 82) to cut bone growth between femoral implant 20 and the femur 28 during the process of insertion. Second impact tool 96 likewise includes a threaded extent 98, a sliding weight 100, and a guide 102. Each impact tool (88, 96) can be manually inserted or can optionally be inserted via a pneumatic hammer.

Figure 18:
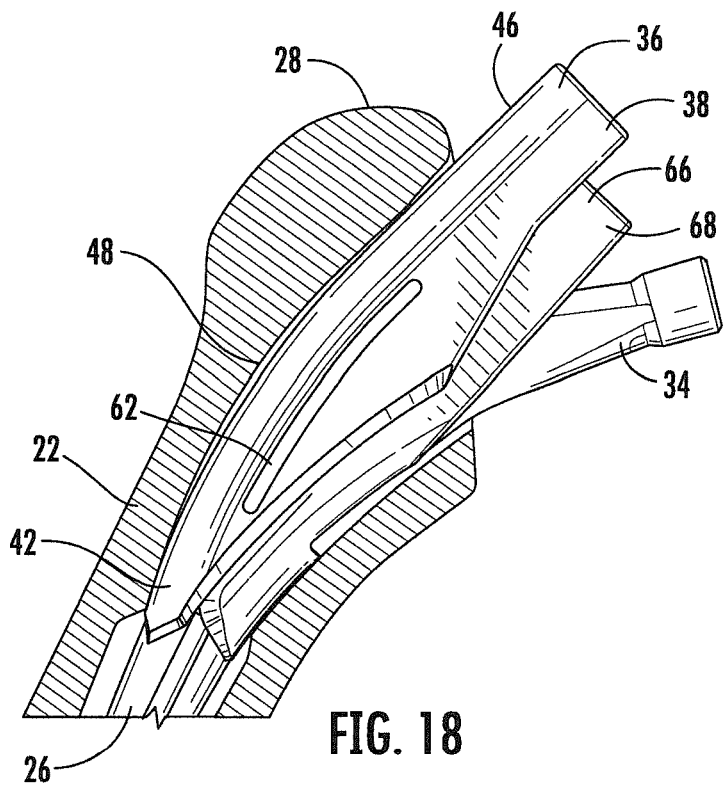
FIG. 18 illustrates the full insertion of both the lateral and medial tools.
Figure 19:
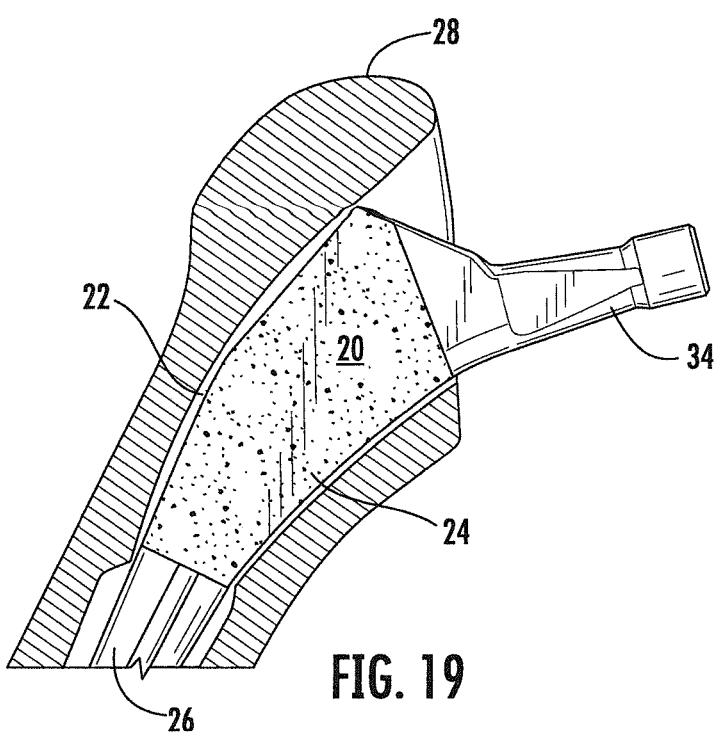
FIG. 19 illustrates the femoral implant following the removal of the lateral and medial tools.

As described, the lateral and medial implant removal tools (36 and 66) can be used in conjunction with one another. It is preferred that lateral tool 36 is inserted and removed prior to the insertion and removal of medial tool 66. FIG. 18 illustrates that in the preferred embodiment lateral and medial tools (36 and 66) are inserted into femur 28 such that the curved extents 58 of lateral tool 36 overlap outer edges 78 of medial tool 66. The overlapping edges (58 and 78) ensure that all bone growth immediately surrounding implant 20 is removed. This ensures the efficient removal of implant 20 with minimal bone loss.

Alternative Embodiments

An alternative embodiment of medial tool 112 is depicted in FIGS. 6-8. This tool 112 is generally the same as medial tool 66 (FIGS. 3-4), but includes a side cut out 114 leading to a narrower distal size when compared to the opening of 188. Medial tool 112 also includes an opening 118 to accommodate different neck geometries and has a lower rounded and sharpened edge 116. This embodiment also includes opposing side walls 124 with inner sharpened edges 122.

Figure 11:
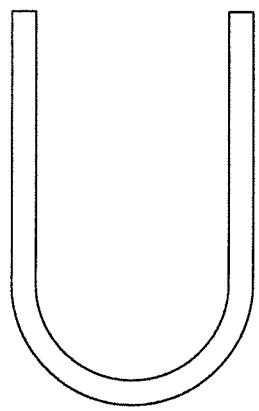
FIG. 11 is a sectional view of the lateral implant removal tool taken along line 11-11 of FIG. 10.
Figure 11A:
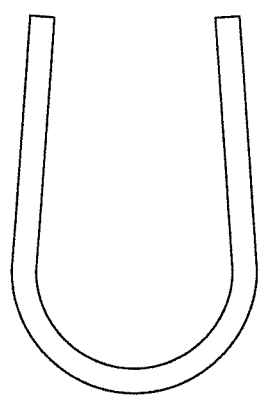
FIGS. 11A-11E are alternative embodiments showing different cross sections of the lateral implant removal tool of FIG. 10, each of which is taken along line 11-11.
Figure 11B:
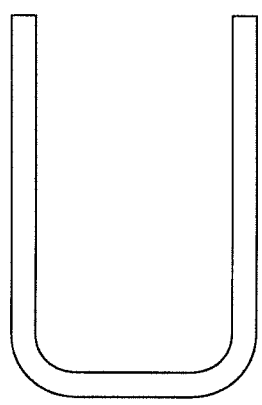
Figure 11C:
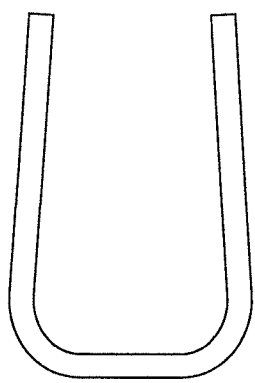
Figure 11D:
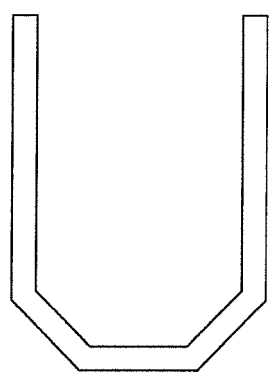
Figure 11E:
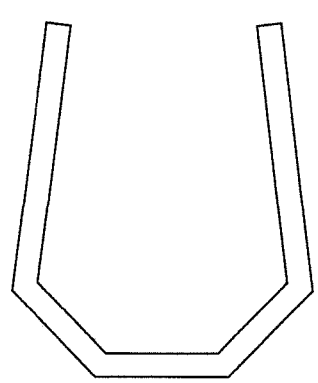
Figure 12:
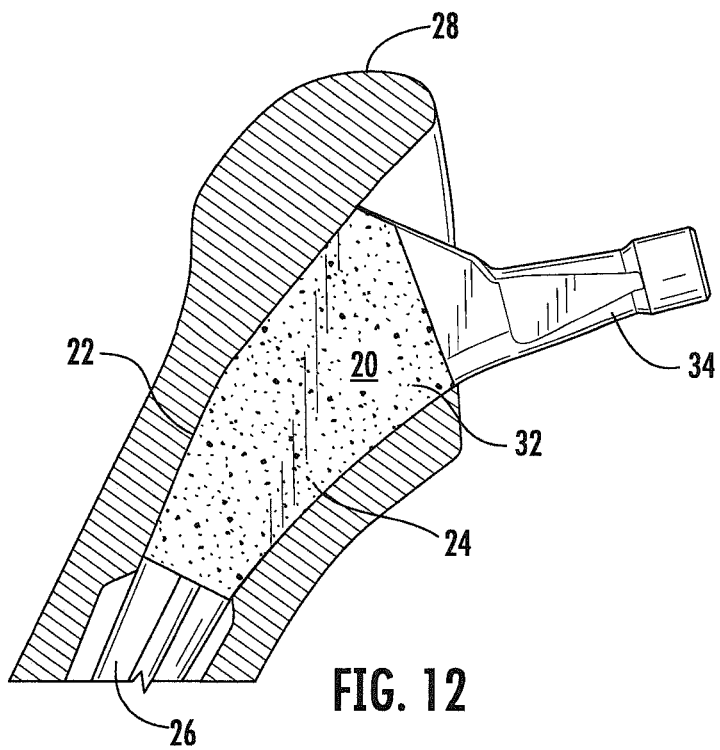
FIG. 12 illustrates a femoral implant prior to the insertion of the lateral and medial tools.

An alternative embodiment of the lateral tool 104 is depicted in FIGS. 9-10. This embodiment is the same in most respects to lateral tool 36. It includes a generally straight back wall 106 and a more curved leading edge 108. This geometry may be preferred for the lateral tool depending upon the shape and size of the implant being removed. FIG. 11 illustrates the U-shaped cross section that makes up the body of this alternative lateral tool 104. However, any of a variety of cross sectional shapes can be used. FIGS. 11a-11e illustrate some possible cross sectional shapes for the lateral tool.

Although this disclosure has been described in terms of certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A system for minimizing bone loss during the removal of a femoral implant, the femoral implant including lateral and medial sides, a stem, an upper textured portion, and a neck, bone growth affixing the upper textured portion to the femur, the system comprising:

a lateral tool including proximal and distal ends and an outer wall with an arcuate extent, the lateral tool further including opposing side walls defining an arcuate interior, each side wall including a first angled extent and a second curved extent, the curved extent being sharpened, a window formed within each of the opposi.ng side walls, a threaded aperture formed within the proximal end, the distal end including a curved and sharpened leading edge, the lateral tool adapted to be inserted between the femur and the lateral side of the femoral implant to thereby separate the textured portion from the femur:

a first impact tool threadably secured to the threaded aperture of the lateral tool, the first impact tool allowing the leading edge and curved extents of the lateral tool to cut bone growth between the femoral implant and the femur;

a medial tool including proximal and distal ends, the medial tool including opposing side walls, with each side wall including inner and outer edges, the outer edges being sharpened, a U-shaped trough with a sharpened leading edge positioned at the distal end of the medial tool, an opening formed through the medial tool, the medial tool adapted to be inserted between the femur and the medial side of the femoral implant with the neck of the implant extending through the opening;

a second impact tool threadably secured to the threaded aperture of the medial tool, the second impact tool allowing the leading edge and the outer edges of the medial tool to cut bone growth between the femoral implant and the femur;

wherein when both the lateral and medial tools inserted into the femur, the curved extents of the lateral tool overlap the outer edges of the medial tool.

2. An implant removal tool for removal of a femoral implant that includes a neck, the tool comprising:

proximal and distal ends and opposing side walls, with each side wall including inner and outer edges, an opening formed through the tool, the tool adapted to be inserted along an edge of the femoral implant with the neck being received within the opening, wherein the opening includes surrounding front and back edges, with all of the surrounding front and back edges being sharpened.

3. The implant removal tool as described in claim 2 further comprising a U-shaped trough positioned at the distal end of the tool.

4. The implant removal tool as described in claim 2 wherein the outer edges of the tool are sharpened.

5. The implant removal tool as described in claim 2 wherein the tool includes a U-shaped trough at its distal end.

6. The implant removal tool as described in claim 5 wherein the U-shaped trough includes a sharpened leading edge.

7. A system for removing a femoral implant, the femoral implant positioned within a femur and including lateral and medial sides, a stem and a neck, the system;

comprising:

a lateral tool including proximal and distalends and an outer wall, the lateral tool further including opposing side walls defining an interior, the lateral tool adapted to be inserted between the femur and the lateral side of the femoral implant;

a medial tool including proximal and distal ends, the medial tool including opposing side walls, with each side wall including inner and outer edges, an opening formed through the medial tool, the medial tool adapted to be inserted between the femur and the medial side of the femoral implant with the neck of the implant extending through the opening, wherein the outer edges of the medial tool are sharpened.

8. The system as described in claim 7 wherein the side walls of the lateral tool include a first angled extent and a second curved extent.

9. The system as described in claim 8 wherein the second curved extent is sharpened.

10. The system as described in claim 7 wherein a window formed within each of the opposing side walls of the lateral tool.

11. The system as described in claim 7 wherein the medial tool includes a U-shaped trough with a sharpened leading edge positioned at the distal end.

12. The system as described in claim 7 wherein with both the lateral and medial tools inserted into the femur, the opposing side walls of lateral tool overlap the outer edges of the medial tool.

* * * * *